(12) United States Patent
O'Donoghue et al.

(10) Patent No.: US 6,663,913 B2
(45) Date of Patent: *Dec. 16, 2003

(54) METHOD OF COATING A BIOACTIVE SUBSTANCE

(75) Inventors: Michael Francis O'Donoghue, Warrandyte (AU); James Allan Morris, Mont Albert (AU)

(73) Assignee: Scientec Research Pty. Ltd., Victoria (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/331,387

(22) PCT Filed: Dec. 22, 1997

(86) PCT No.: PCT/AU97/00872

§ 371 (c)(1),
(2), (4) Date: Jul. 2, 1999

(87) PCT Pub. No.: WO98/27927

PCT Pub. Date: Jul. 2, 1998

(65) Prior Publication Data

US 2002/0001667 A1 Jan. 3, 2002

(30) Foreign Application Priority Data

Dec. 20, 1996 (AU) .............................. PO 4315

(51) Int. Cl.⁷ .............................. A61J 3/00; A61K 9/00; B05D 1/34
(52) U.S. Cl. ...................... 427/2.14; 427/2.1; 427/212; 427/213.3; 427/213.31; 427/213.35; 427/214; 427/355; 427/356; 118/35; 118/36; 118/40

(58) Field of Search ................................. 427/2.14, 2.1, 427/212, 213.3, 213.31, 213.35, 214; 118/35, 36, 40, 355, 356

(56) References Cited

U.S. PATENT DOCUMENTS

| | | | |
|---|---|---|---|
| 4,892,538 A | | 1/1990 | Aebischer et al. |
| 5,451,424 A | * | 9/1995 | Solomon et al. .............. 427/2.1 |
| 5,643,773 A | * | 7/1997 | Aebischer et al. .......... 435/182 |
| 5,890,955 A | * | 4/1999 | Stanley ........................ 452/48 |
| 6,010,715 A | * | 1/2000 | Wick et al. .................. 424/448 |
| 6,045,848 A | * | 4/2000 | Quinones et al. ........... 426/513 |

FOREIGN PATENT DOCUMENTS

| | | |
|---|---|---|
| GB | 2099699 | 12/1982 |
| JP | 59-216802 | 12/1984 |
| JP | 6-321803 | 11/1994 |
| WO | WO95/23598 | 9/1995 |

* cited by examiner

Primary Examiner—Shrive P. Beck
Assistant Examiner—Jennifer Kolb Michener
(74) Attorney, Agent, or Firm—Roylance, Abrams, Berdo & Goodman, LLP.

(57) ABSTRACT

The invention generally provides a method of coating a material, the method including the following steps: (a) forming a generally elongate coating structure (15), the coating structure having an internal cavity (17) extending at least substantially along its length, and wherein the internal cavity of the coating structure is capable of receiving a core material (21); (b) inserting a core material (21) into the internal cavity (17) of the coating structure (15); (c) compressing the coating structure at a first location (44) along its length so as generally to form a seal at that location; and (d) compressing the coating structure at a second location along its length (45).

22 Claims, 4 Drawing Sheets

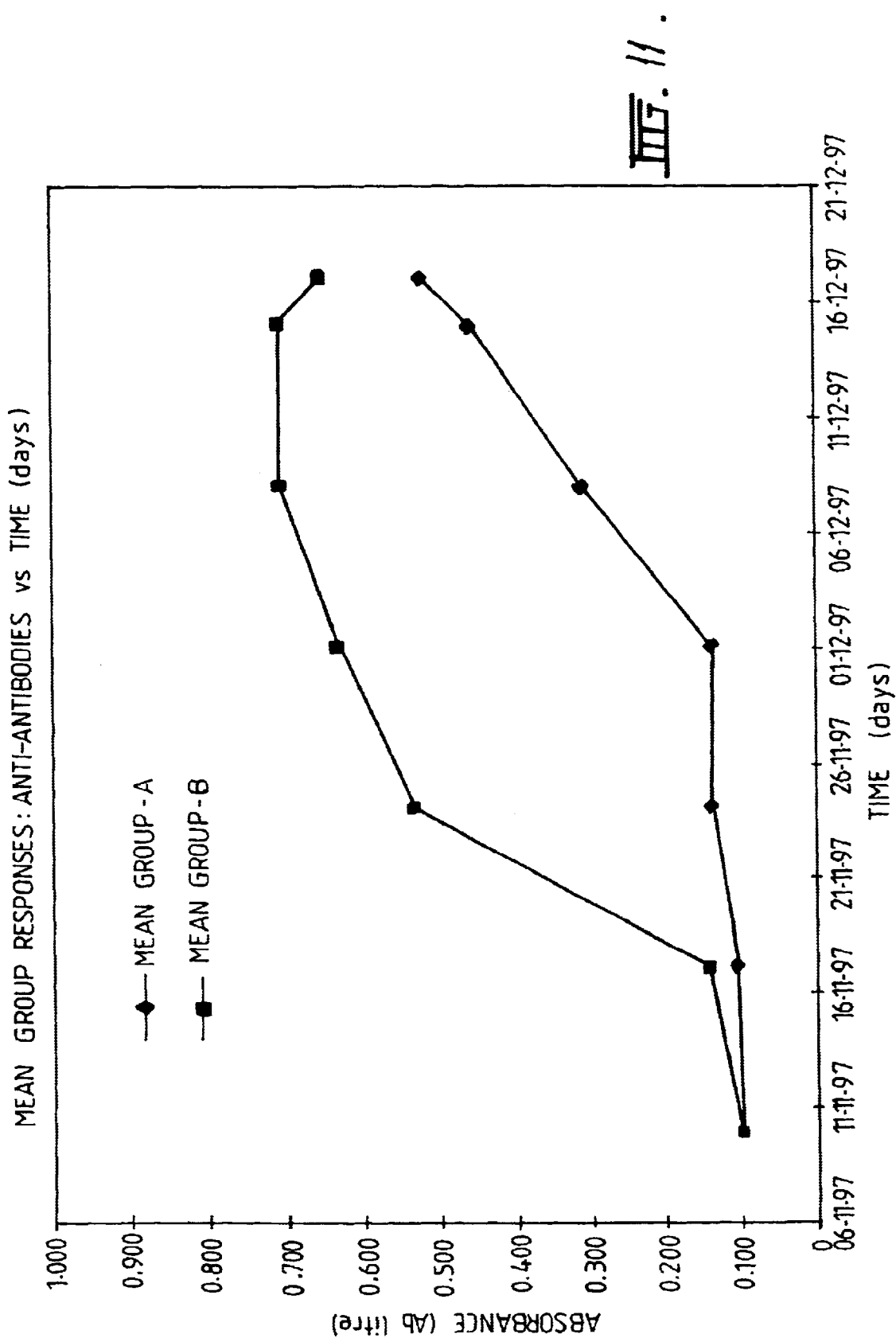

METHOD OF COATING A BIOACTIVE SUBSTANCE

INTRODUCTION

This invention relates to apparatus and methods for coating a material. As will become apparent from the following description, the invention can be used in many coating applications, however one application to which the invention is particularly suited is in relation to the production of coatings for pharmaceutical capsules, tablets and like devices for the delivery of pharmacologically active substances (for either human or veterinary use) to a patient. The invention is especially suited for use in the production of pharmaceutical capsules, tablets and like delivery devices where the coating material for the pharmaceutical delivery device is intended to control or delay the timing of release of a pharmacologically active material contained within the "core" of the device. While noting the invention's suitability in a broad range of applications, it will be described in the following description with particular reference to the pharmaceutical coating application to which it is particularly suited.

BACKGROUND TO THE INVENTION

In order for an effective dosage regimen to be delivered, many pharmaceutical substances must be administered according to exacting or occasionally, complex dosage regimes. Compliance with such regimes is particularly important in, for example, many third world countries, where patient compliance with a dosage regimen may be impaired due to the patient's inability to understand the nature of the dosage regimen required, or the need for compliance. Similarly, the treatment of infants by a repeated course of injections can be particularly traumatic to the infant patients concerned, and the delivery of the regimen by a reduced number of doses whose release profile is controlled is particularly desirable. Another important scenario where controlled release delivery can be particularly advantageous (compared to repeated application of individual doses) is in veterinary medicine. Many animals react extremely adversely to the infliction of pain by (for example) repeated injections. In the veterinary treatment of animals, it can be particularly difficult to ensure that the animal has received the dosage required of the pharmaceutical agent concerned (particularly, for example, if the pharmaceutical agent involved must be administered in minute quantities, such as, for instance, with reproductive hormones used in animal husbandry). Repeated handling of an animal to administer drugs to it not only runs the risk that the animal will refuse to co-operate with the handler, and that the required dose of the drug may not in fact be delivered, but also, it runs the increased risk of injury to the animal handler that must administer the drugs.

The use of controlled release pharmaceutical delivery devices is therefore particularly desirable in many instances, including those described above. However, the delivery of drugs via controlled release regimens is not as widespread as might be hoped, because the production of suitable delivery devices for the controlled release of pharmacologically active substances is presently limited by the manufacturing methods 3 and production apparatus that have been used to date to make them.

Several methods have been employed to date in order to manufacture controlled release delivery devices to contain a dose of a pharmaceutical agent in the form of (for example) a tablet. One method that has been employed is injection moulding. This technique involves the injection of a heated coating material (typically, a pharmaceutically acceptable polymer) under pressure into a mould for a delivery device (in the form of, for example, part of a container). Once the coating material has cooled and solidified to a suitable extent, the mould is opened for ejection. The part container must then be filled with the pharmaceutical agent it is intended to contain, and it must then be sealed. This technique has significant limitations, particularly for the mass production of controlled release pharmaceutical delivery devices. For one thing, as explained above, it results in the production of only a partial container. This means that the process of producing a controlled release drug delivery device via the injection moulding method is a multi-step procedure, which requires sequentially (i) first, the production of a partial container, (ii) filling the partial container with the required dose of the drug it is intended to contain, and (iii) then sealing the container. This sequential, multi-step procedure is inefficient as a manufacturing process. It also involves a time delay between the initial step of manufacturing the partial-container and the subsequent steps of filling it with the pharmaceutical moiety and sealing the container, which can give rise to difficulties as regards ensuring that the finished product is sufficiently sterile for use in human or veterinary medicine.

A second technique is available for manufacturing pharmaceutical delivery devices in such a way as to overcome the sterility problems described earlier that affect the injection moulding procedure. In the pharmaceutical context, to date, the second technique appears to have been used solely in the manufacture of sterile vessels to contain liquids like physiological saline or water for injection. This second technique is referred to in the art as the "blow-fill-seal" (or the "form-fill-seal") method. In this technique, a polymer (usually a plastics material) is melt-processed and extruded from a die to form a length of tube. When extruded, the tube is sufficiently hot to be malleable, but not so hot as to be liquid, and therefore, so as to be uncontrollable in the subsequent steps involved in the manufacturing process. A multi-piece die (containing a mould which encompasses the length of extrudate) then clamps around the length of extrudate (which is known as the "parison"), thereby sealing one end of the parison, and leaving the other end gripped by the die, but slightly open. The parison (which at this stage of the process, remains hot and malleable) is a thin tube which is suspended within the mould cavity. Air is then injected into the interior of the parison so as to inflate it, so that it assumes the shape of the mould. The inflated parison is then filled with the desired contents by an injection process, and is then sealed. The die is then opened to release the finished product. The "blow-fill-seal" technique is similar in many respects to injection moulding. It is therefore subject to at least some of the same problems that apply to the injection moulding technique.

The present invention aims to avoid one or more difficulties associated with the prior art manufacturing techniques described above, and the apparatus used to perform them.

GENERAL DISCLOSURE OF THE INVENTION

The invention generally provides a method of coating a material, the method including the following steps:

(a) forming a generally elongate coating structure, the coating structure having an internal cavity extending at least substantially along its length, and wherein the internal cavity of the coating structure is capable of receiving a core material;

(b) inserting a core material into the internal cavity of the coating structure;

(c) compressing the coating structure at a first location along its length so as generally to form a seal at that location; and (d) compressing the coating structure at a second location along its length.

The method may be performed sequentially in the order of steps (a) to (d) set out above, or the steps of the method may be performed in another sequence. A preferred sequence is (from first to last step):

Step (a) (first step)
Step (c) (second step)
Step (b) (third step)
Step (d) (fourth step).

Preferably, the step of forming the coating structure involves extruding it from an extrusion means. In this embodiment of the invention, the coating structure must be an extrudable material, such as a plastics material which is amenable to processing techniques such as melt-processing and extrusion when heated. The extrusion means could for example, take the form of a die which extrudes the coating structure in lengths of any desired cross-sectional shape. Preferably, the cross-sectional shape of the coating structure formed by the extrusion means is circular, so that in its three-dimensional configuration, the coating structure generally has the appearance of a tubular structure. The coating structure's cross-sectional shape could take any desired form however, including generally square, triangular, elliptical, ovoid or more complex shapes. The proviso here is that the cross-sectional shape must be a closed shape (such as the shapes described earlier), so that the extruded coating structure can be sealed when it is subjected to the compression steps of the method, described earlier. The cross-sectional shape adopted for the coating structure in any context may depend on the application to which the coated material produced by the coating method is to be put.

In one form of the invention, the coating structure comprises a single layer of the material from which it is formed. In other forms of the invention however, the coating structure may contain two or more layers of the same or of different materials from which it is formed. Forming the coating structure from two or more layers may be preferred where it is desired to control in a particular manner, the release profile of the core material from a finished container produced by the method. By forming the layers of the coating structure from materials having different degradation or permeability characteristics, a differential rate, onset or profile of release of the core material into a surrounding environment, as desired, could therefore be established.

Preferably further, in step (d) of the method, a seal is formed at the location of the second compression along the length of the coating structure, so as to define a closed container which comprises the coating structure sealed at two opposed ends, and containing the core material in its internal cavity. Preferably, the seal at each end of the container is formed by compressing two mutually opposed surfaces of the coating material so that they come into contact with one another in a sealing manner. A seal at any location could also be formed in other ways however, such as by heating the coating structure in addition to compressing it at the location concerned. The step of compressing the coating structure at any location could also involve cutting the coating structure at each of the first and second locations along its length, so as to define a free-standing container separated from the remaining coating structure from which the container was formed. Preferably further, such a container would have the appearance of a capsule, such as that of a conventional pharmaceutical capsule.

In some applications, it might be desirable to produce a container which is sealed at one end, but not at the other. In such a case, in step (d) of the method, the step of compressing the second location along the length of the coating structure could take the form of simply cutting it by using a cutting means, rather than forming a seal at that end. This version of the method might be used so as, for example, to form a pharmaceutical delivery device having one sealed end and one "open" end, so as to provide a delivery device which in use, would encourage the egress of the core material into a patient, from the "open" end of the device.

In other applications, it may be preferred to form a container which is completely unsealed at one end, and is "generally" sealed at the other. By "generally" sealing the container at the other end (meaning the first location along the length of the coating structure, in the description set out herein), and further, by reference in step (c) of the first aspect of the invention, mentioned earlier, to "generally forming a seal", it is to be understood that a closure which falls somewhat short of a full or complete seal, is also comprehended. Thus, the formation of a partial seal at that location would be embraced by this feature of the invention.

Preferably further, the method would be suitable for continuous operation, or for repeated operation, along the length of the coating structure. In this way, the method C could be used to generate a desired number of individual containers each containing a length of the coating structure which are sealed as desired, and each of which contains an amount of the core material in its internal cavity. It is even further preferred that automation means be provided to operate the method, so that a convenient integrated method is provided for producing a desired number of containers as described above.

In a particularly preferred embodiment of the invention, the method is used to produce pharmaceutical delivery devices, such as coated capsules, coated tablets and the like. In this embodiment of the invention, the coating structure takes the form of a pharmaceutically acceptable substance or combination of such substances. Typically, the coating will comprise a pharmaceutically acceptable polymer or co-polymer, such as a plastics material. Particularly preferred substances for the coating material include polylactide-co-glycolide polymers, polyesters, polysaccharides, polyamides, poly (amino acids), poly (ortho esters), polyanhydrides, polyphosphoesters and polymers formed through combinations of chemical bonds (such as pseudo-peptides, poly (phosphoester-urethanes) and polydepsipeptides). The core material, in this embodiment of the invention, contains the pharmacologically active substance (for convenience called the "bioactive" in the remainder of this specification) whose release profile is desired to be controlled by the provision of the coating structure. The bioactive can be any suitable pharmacologically active substance. Typically, the bioactive would be a hormone or a vaccine, although the method is applicable to producing pharmaceutical delivery devices suitable for a broad range of bioactives, including natural, synthetic or recombinant pharmacological agents, food additives or food supplements, antigens, antibodies, cytokines, growth promotants, hormones, cancer cell inhibitory agents, immuno-suppressants or immuno-stimulants, anti-microbial agents (including antibiotics), anti-viral agents, vitamins, vaccines, minerals, and organic or inorganic nutrients. A bioactive core material for use in the invention may consist of one type of the aforementioned substances, or may include combinations of two or more such substances.

The bioactive (or a composite core material in which it is contained) could also take any number of physical forms, such as in the form of a tablet, a gel, a paste, as granules, in powder form, or a fluid, as well as others. The core material could also contain additional materials to the bioactive itself, including pharmaceutically acceptable carriers and excipients (including dispersion media, coatings, antibacterial, anti-fungal and/or anti-viral agents and the like, as well as salts such as di-calcium phosphate), inert (and pharmaceutically acceptable) materials designed to control further the release of the bioactive in a desired manner, and other like materials, as desired. For example, the core material could also contain a hydrophilic material to encourage the entry of water into the device (such as for example, a swelling agent, such as a "hydrogel") or a substance affecting the osmotic interaction of the core material with an external biological fluid. Additional components could include:

(i) binders, such as gum tragacanth, acacia, corn starch or gelatine;

(ii) disintegrating agents, such as corn starch, potato starch, alginic acid and the like;

(iii) lubricants, such as magnesium stearate;

(iv) explosive combinations (eg, citric acid/sodium carbonate);

(v) surfactant materials or other surface active molecules (eg, proteins, such as albumins, biological detergents and tweens);

(vi) solubility enhancers (eg, sodium citrate, sodium bicarbonate, magnesium carbonate);

(vii) absorbance enhancing agents;

(viii) lubricants;

(ix) flow promoters;

(x) plasticisers;

(xi) antisticking agents: and/or (xii) anti-static agents.

As would be apparent to those skilled in the art, in pharmaceutical applications of the invention, all such additional components must be at least substantially pharmaceutically pure, non-toxic in the amounts used, and biocompatible with the bioactive(s) used and with the coating material.

The invention also provides an apparatus for coating a material, the apparatus including:

(a) means for forming a generally elongate coating structure having an internal cavity extending at least substantially along its length, and wherein the internal cavity of the coating structure is capable of receiving a core material;

(b) means for inserting a core material into the internal cavity of the coating structure;

(c) means for compressing the coating structure at a first location Q along its length so as generally to form a seal at that location; and (d) means for compressing the coating structure at a second location along its length.

Preferably, the means for forming the elongate structure are extrusion means, as discussed earlier.

As explained above, the core material could take any number of physical forms, such as in the form of a tablet, a gel, a paste, as granules, in powder form, or as a fluid, as well as others. The means for inserting the core material into the coating structure could therefore take any number of forms, according to the nature of the core material to be inserted into the coating structure. For example, where the core material takes the form of a gel or paste, the means for inserting it into the coating structure could take the form of a nozzle designed to inject the core material into the internal cavity of the coating structure.

The means for compressing the coating structure at the first location could, for example, take the form of a mechanism for simply pressing two opposed surfaces of the coating structure together. Such means could also include means for forming a cut through the coating structure at that location. The means for compressing the coating structure at the second location could also take a similar form, however they could, if desired, take the form of a mechanism for forming a non-sealing open cut at the second location, so as to form a capsule with an open end at the second location.

Preferably, the apparatus is suitable for continuous, or repeated operation along the length of the coating structure, so as to lend itself to mass production of segments of a coated material, in the form of capsules or like devices.

The invention further provides a coated material produced by a process which includes the steps of:

(a) forming a generally elongate coating structure, the coating structure having an internal cavity extending at least substantially along its length, and wherein the internal cavity of the coating structure is capable of receiving a core material;

(b) inserting a core material into the internal cavity of the coating structure;

(c) compressing the coating structure at a first location along its length so as generally to form a seal at that location; and (d) compressing the coating structure at a second location along its length.

Preferably, the coated material produced by the process takes the form of a coated tablet, coated capsule or a like device. Preferably further the coated structure is suitable for use as a controlled release device for delivering an amount of the core material in a predetermined manner. It is particularly preferred that in such a device, the core material contains a pharmacologically active substance, such as any of the bioactives described earlier. The process could also be configured to produce a coated material containing multiple units of the same bioactive, or a two or more units of different bioactives.

BRIEF DESCRIPTION OF THE DRAWINGS

The invention will now be described by way of example only with reference to the following drawings, in which:

FIG. 11 is a graph which charts the results of an experiment performed in rats to measure the controlled release (delay) of a bioactive formulation made in accordance with the invention, relative to a control group.

DETAILED DESCRIPTION OF PREFERRED EMBODIMENTS OF THE INVENTION

Figure 1A:
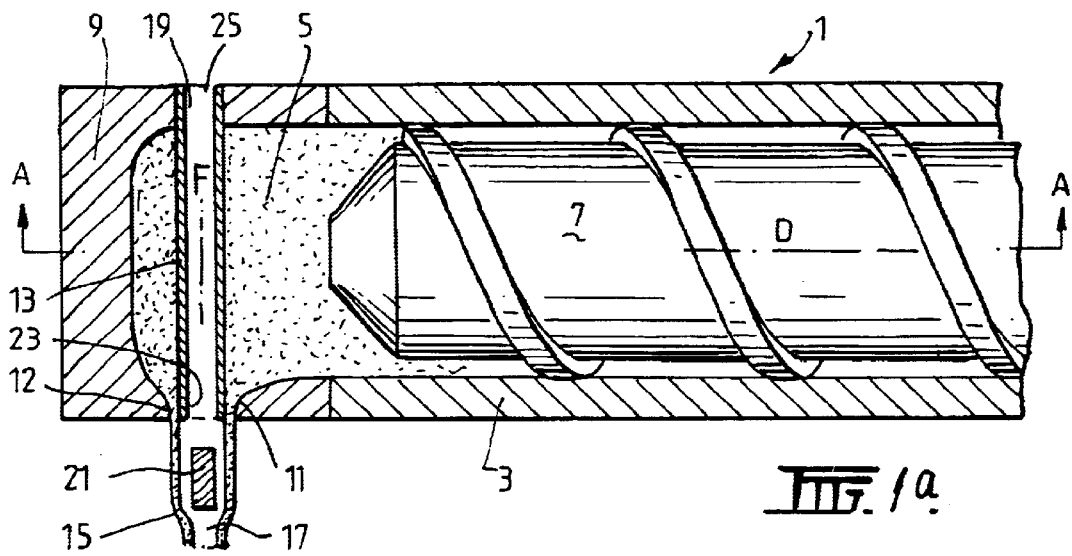
FIG. 1a represents a side cross-sectional view of an apparatus constructed in accordance with the invention, for use in coating a material.

Referring now to the drawings, FIG. 1a shows an apparatus (generally denoted 1) for coating a material, constructed in accordance with a first embodiment of the invention. Apparatus 1, which is shown in cross section from the side, is an apparatus which could be used for coating capsules, such as pharmaceutical capsules. As can be seen from FIG. 1a, apparatus 1 consists of an extruder barrel (generally denoted 3), having an internal bore 5, and a threaded extruder screw 7 located and supported for rotation inside the bore 5, by any suitable means, such as those that would readily understood by persons skilled in the art.

The extruder barrel 3 includes a cross head die 9 near its distal extremity. In use of apparatus 1, a flowable coating material is placed in bore 5, and by rotating extruder screw 7 about its longitudinal axis D within bore 5 in a direction so as to convey the flowable coating material towards the cross head die 9, is extruded from an opening 11 on the cross head die. The cross head die 9 includes an extrusion sleeve 13, whose longitudinal axis F is at right angles to the longitudinal axis D of the extruder screw 7. As shown more particularly in FIG. 1b, extrusion sleeve 13 is of generally circular shape when viewed in cross-section, in the embodiment of the apparatus shown. When the extruder screw 7 is rotated within bore 5, this motion causes agitation of the flowable coating material so that it is moved towards and onto the outer surface 12 of extrusion sleeve 13, from within bore 5. Ultimately, such agitation causes the flowable material to exit from the opening 11 (which, by virtue of the cross sectional shape of extrusion sleeve 13, means that in the embodiment shown in FIGS. 1a and 1b, opening 11 is a generally annular opening). This in turn results in an elongate, generally tubular coating structure 15, formed from the flowable material, being extruded from the apparatus, as shown in FIG. 1a. This generally tubular coating structure can be used to coat a material within its internal cavity 17, which generally takes the form of a lumen.

Figure 1B:
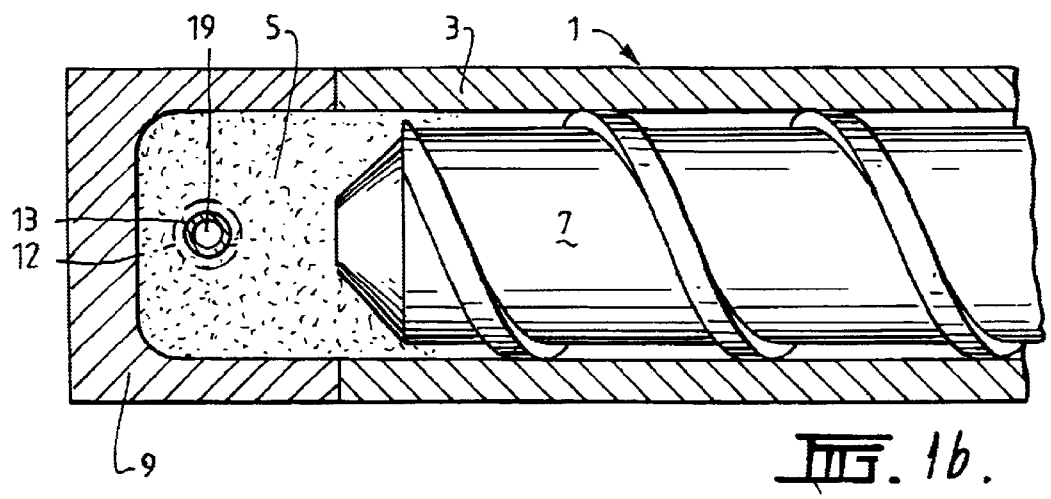
FIG. 1b represents a cross section of the apparatus depicted in FIG. 1a, taken along the line A—A, and when viewed in the direction of the arrow B.

As shown more particularly in FIG. 1a, extrusion sleeve 13 has an internal bore 19. This internal bore is designed to receive a material 21 (which in FIG. 1 is shown as being in the form of a generally cylindrical tablet or pellet) within it, so that material 21 may be conveyed to the end 23 of the extrusion sleeve, where it is enters the cavity 17 and is encapsulated by the generally tubular coating structure 15. In the embodiment of the apparatus 1 shown in FIGS. 1a and 1b, the extrusion sleeve is configured so that the material 21 to undergo coating is fed into the internal bore 19 from an upwardly disposed end 25 of the extrusion sleeve, so that it falls within the extrusion sleeve's internal bore under the influence of gravity, so as to be conveyed to and to exit from the lower end of the extrusion sleeve, for coating by the generally tubular coating structure. In other embodiments of the invention, the extrusion sleeve might not be so disposed within the apparatus, and means other than gravity could be used to convey the material 21 to the coating point. Those skilled in the art would readily understand that such means could take any number of forms. In the embodiment of the invention shown in FIGS. 1a and 1b, the material 21 to undergo coating is fed into the generally tubular coating structure 15 in the same direction as the egress of that structure from the apparatus 1. In this specification, an arrangement whereby the direction of feed of the coating material is the same as the direction of egress of the coating structure from the general forming apparatus is termed "rear loading".

Figure 2:
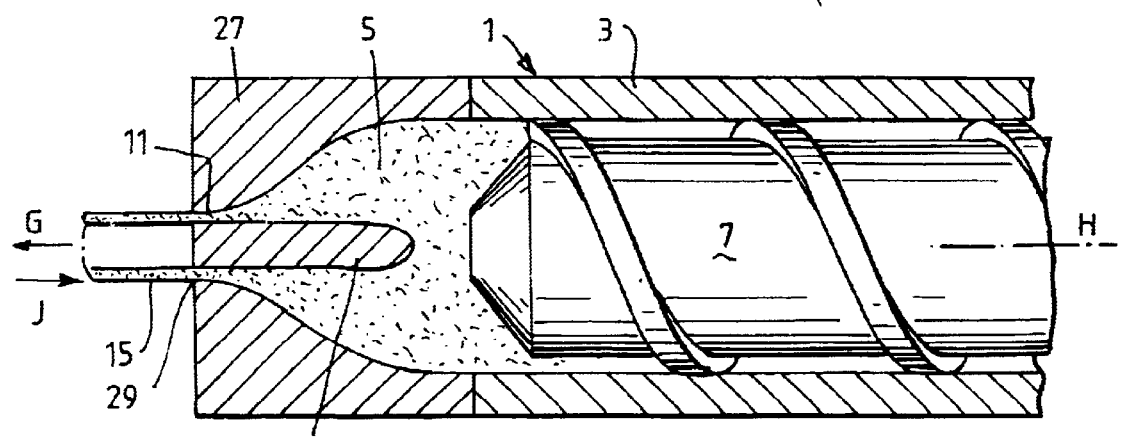
FIG. 2 represents a side cross-sectional view of a second apparatus for coating a material, constructed in accordance with the invention.

A different embodiment of an apparatus for coating a material and a coating method in accordance with the invention is shown in FIG. 2. In the description that follows, for ease of reference and comparison, features depicted in the embodiments described hereafter that correspond to similar features depicted in FIGS. 1a and 1b will be accorded the same reference numerals. In FIG. 2, the apparatus (also generally denoted 1) also includes an extruder barrel 3, having an internal bore 5 and an extruder screw 7, as in the first embodiment of the invention discussed earlier. However, in this embodiment, the end of the extruder barrel takes the form of a tube die 27, rather than a cross head die. In this embodiment, the flowable coating material is extruded from an opening 11 located at the end of the apparatus 1, so that it is extruded in the direction of the arrow G shown in FIG. 2, that is, in a direction generally parallel to the longitudinal axis H of the apparatus 1. The opening 11 from which the flowable coating material is extruded is also circular in shape, when viewed in the direction of the arrow J shown in FIG. 2. Opening 11 is an annular hole defined by a circular aperture in the end wall 29 of the apparatus 1, and by a circular forming means 31 located within that circular aperture. The circular aperture 29 and the forming means co-operate so that the flowable coating material is extruded as a generally tubular coating structure from the opening 11. A material 21 to be coated is positioned ahead of the direction of flow of the coating structure 15 so as to be fed into, or is fed into the internal cavity 17 of that structure by movement in a direction opposite to the direction of egress of the coating structure 15 from apparatus 1. In this specification, such an arrangement for coating a material with the coating structure formed within apparatus 1 is termed "front loading".

Figure 3:
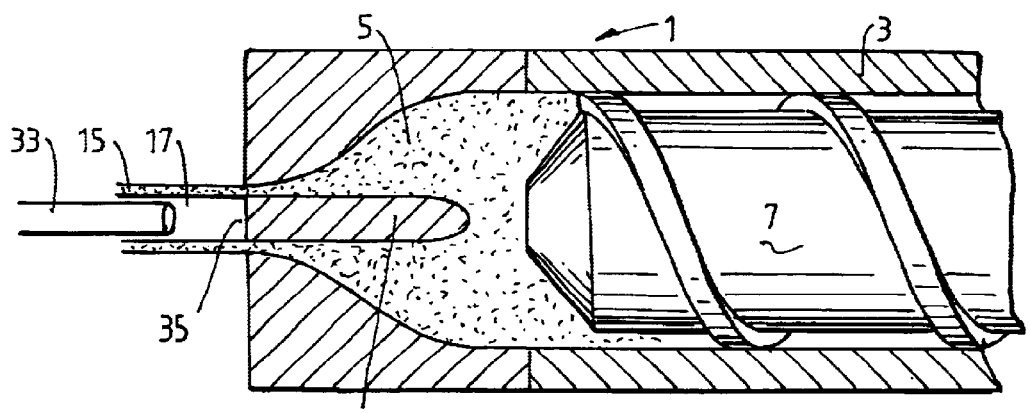
FIG. 3 depicts a modified version of the embodiment of the invention shown in FIG. 2.

A further, slightly modified version of a front loading coating apparatus constructed in accordance with the invention, is shown in FIG. 3. The apparatus is substantially the same as that depicted in FIG. 3, except that it also includes the use of an additional forming means 33, which in the embodiment shown, takes the form of a generally tubular structure which is adapted to enter the cavity 17 of the generally tubular coating structure 15. A material 21 to be coated is introduced into the lumen 35 of the tubular forming means 33, and conveyed by any suitable means (such as, for example, by an injection of air into the lumen at the opposite end of the forming means 33) to place the material 21 within the coating structure, so as to coat the material. The forming means 33 would desirably be readily retractable from the tubular coating structure 15.

The embodiments of the method described above each involve the initial step of forming a generally elongate coating structure (in the form of the generally tubular coating structure 15), via a forming means. Generally, an extrusion process would be best suited for this purpose, although other methods of forming the coating structure may be used in the invention. Where an extrusion process is used, the material used to form the coating structure must be amenable to manipulation by processes such as melt-processing, so that the material can be suitably extruded from the forming apparatus to give rise to the coating structure in the desired conformation. For pharmaceutical applications, suitable materials would generally include pharmaceutically acceptable polymers, such as pharmaceutically acceptable plastics. Examples of pharmaceutically acceptable polymers would include polylactide-co-glycolide polymers, polyesters, polysaccharides, polyamides and poly (amino acids), poly (ortho esters), polyanhydrides, polyphosphoesters and polymers formed through combinations of chemical bonds (such as pseudo-peptides, poly (phosphoester-urethanes) and polydepsipeptides). Other suitable materials could be used, the nature of which would be apparent to those skilled in the art.

In each of the embodiments described earlier, the method involves the second step of inserting the core material into the internal cavity of the coating structure. The nature of the core material will vary in accordance with the nature of the application to which the invention is to be put. In pharmaceutical applications, the core material will generally contain a bioactive. A broad range of hormones, including both steroid and non-steroidal hormones, and many types of vaccines, would constitute suitable bioactives for this purpose.

In pharmaceutical applications of the invention, the bioactive would often be included as part of a composite core material, which could take any number of physical forms. For example, the bioactive could be contained in the form of a tablet, a gel, a paste, as granules, in powder form, as well as combinations of the foregoing, and other physical forms. In pharmaceutical applications, the core material would often contain additional substances to the bioactive itself, including pharmaceutical excipients, inert (and pharmaceutically acceptable) materials which might be designed to control the release of the bioactive in a particular manner, and other like materials, as desired. Examples of additional materials which could be contained within the core material include hydrophilic materials to encourage the entry of water into a coated pharmaceutical delivery device (such as for example, swelling agents, such as a "hydrogel") could be used for this purpose, as could substances affecting the osmotic interaction of the core material with an external fluid (such as a biological fluid). Additional components include:

(i) binders, such as gum tragacanth, acacia, corn starch or gelatine;
(ii) disintegrating agents, such as corn starch, potato starch, alginic acid and the like;
(iii) lubricants, such as magnesium stearate;
(iv) explosive combinations (eg, citric acid/sodium carbonate);
(v) surfactant materials or other surface active molecules (eg, proteins, such as albumins, biological detergents and tweens);
(vi) solubility enhancers (eg, sodium citrate, sodium bicarbonate, magnesium carbonate);
(vii) absorbance enhancing agents;
(viii) lubricants;
(ix) flow promoters;
(x) plasticisers;
(xi) antisticking agents; and/or
(xii) anti-static agents.

As explained earlier, and as would be apparent to those skilled in the art, in pharmaceutical applications of the invention, all such additional components must be at least substantially pharmaceutically pure, non-toxic in the amounts used, and biocompatible with the bioactive(s) used and with the coating material.

The means employed for inserting the core material into the internal cavity of the coating structure will also depend upon the nature of the core material adopted in any particular application. Generally, the means for inserting the core material into the coating structure will include a chute or nozzle into which the core material is introduced, and by which it is inserted into the coating structure. Such means could also include apparatus for pushing the core material into a desired position within the coating structure (eg, an injection of air to convey the core material to, or to position the core material in place in the coating structure). If the core material is a tablet, it could be deposited into position with, for example, a pushrod which retracts clear of the coating structure prior to its compression by a compression means. Where the core material in the form of a liquid, paste, granules or in a powder form, the means for inserting it into the coating structure may take the form of an injection apparatus to inject it into the coating structure as appropriate. The injection mechanism used would be designed so as to be retractable from the coating structure prior to any compression step occurring.

Where the coating structure has been formed by melt-processing and extrusion, it may be necessary to cool the extrudate so that it solidifies to a suitable extent to enable the core material to be loaded into it, and at the same time, not damaged. Any suitable means (such as those that would be apparent to persons of ordinary skill in the art) could be used for this purpose. It is particularly desirable that the cooling processes cool the extrudate at such a rate so that when the time comes for the core material to be inserted into it. It has cooled to a sufficient extent to be able to receive the core material safely.

The third step of the production method involves the step of compressing the coating structure at a first location along its length so as generally to form a seal at that location. The purpose of compressing the coating structure is to compress, seal and (where appropriate), to cut the coating structure at the point where compression occurs. Examples of apparatus that could be used to perform the first compression step are depicted in FIGS. 5(a) to (c) and FIGS. 6(a) to (c). The apparatus depicted in FIGS. 5(a) to (c) take the form of a "scissors" apparatus (generally denoted 35, which includes a pair of blades 37 adapted to slide across one another. The widest section of the compressed area along the coating structure should not exceed the outside diameter of that structure.) Thus, the provision of notches (such as the notches 39 shown in FIGS. 5(a) to (c)) would ensure that the area of compression on the coating structure is not greater in section than the cross-sectional diameter of that structure.

Figure 6:
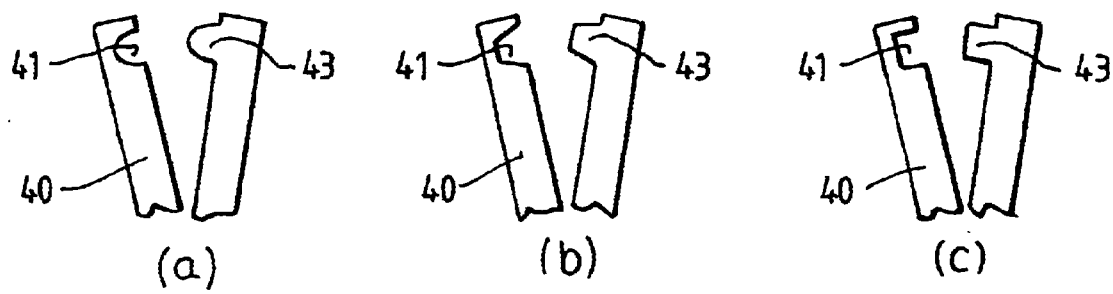
FIGS. 6(a) to (c) depict three further embodiments of a forming apparatus for use in the invention.

The means for compressing the coating structure at either the first and/or second locations in the process could alternatively take the form of a "plier" mechanism, where two blades meet one another. FIGS. 6(a) to (c) depict three examples of possible mechanisms for achieving such a compression action. As can be seen, in FIGS. 6(a) to (c). one blade (denoted 40 in each of those drawings) includes a concave recess 41, whereas its opposed blade includes a mating protrusion 43. In use of such plier apparatus in conjunction with the invention, after the step of inserting the core material into the coating structure has occurred in the production method, the filled coating structure would be passed through the concave part of the plier means, and the two blades would be brought together so as to cut through the filled coating structure. By virtue of the mating fit of the two blades, the cut formed would not have a sectional diameter exceeding the cross-sectional diameter of the coating structure.

A third possible compression means would take the form of a plier action with two blades, where one or both blades have a cutting edge which is not sharp. Such a mechanism would simply compress, rather than cut the filled coating structure, and in some applications may be necessary, in combination with a cutting means, to achieve a seal on the filled coating structure. Whichever form of compression apparatus is used, it could either be free-standing (and capable, if desired, of being manually operated), or more desirably for automated mass production systems, it would be integrated into, and form part of an integrated apparatus for carrying out the method aspects of the invention.

Figure 10:
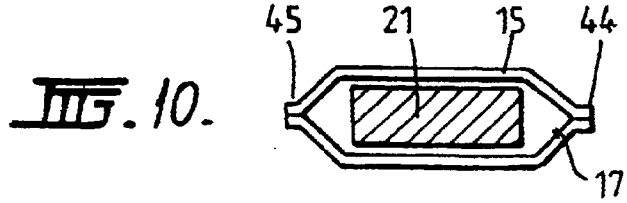
FIG. 10 is an enlarged schematic view of a coated capsule made in accordance with the invention.

When the filled coating structure is compressed so as to cut it at two locations along its length, a separated segment of the filled coating structure is formed. As shown in FIG. 10, in a preferred embodiment of the invention, the segment formed by this method includes a sealed outer layer (consisting of the coating structure (15), which is sealed upon itself at each of points 44 and 45, so as to define a capsule which includes a core material 21, within its internal cavity 17. The sealing of the capsule formed by this process could also be achieved by means additional to those described above (eg. by heating the capsule at each of its ends).

Figure 4:
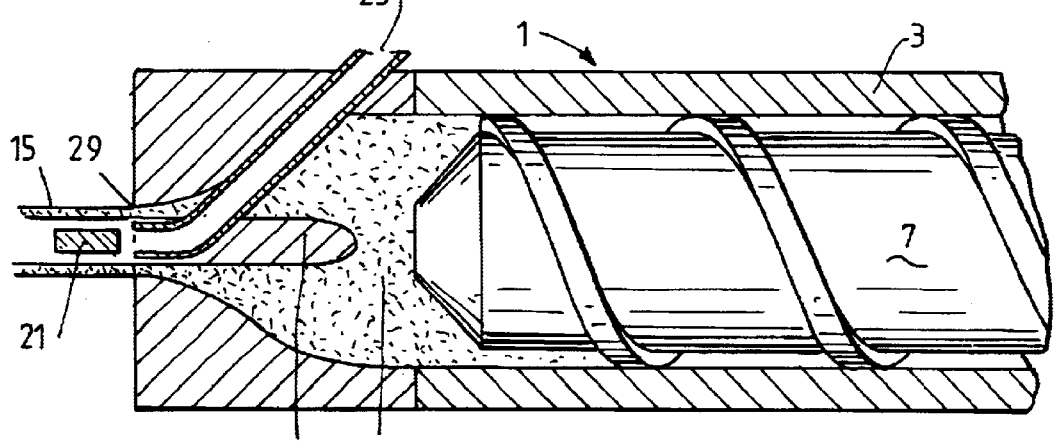
FIG. 4 represents a rear loading forming apparatus constructed in accordance with a fourth embodiment of the invention (being an enlarged view of part of the apparatus depicted in FIGS. 7–9)
Figure 5:
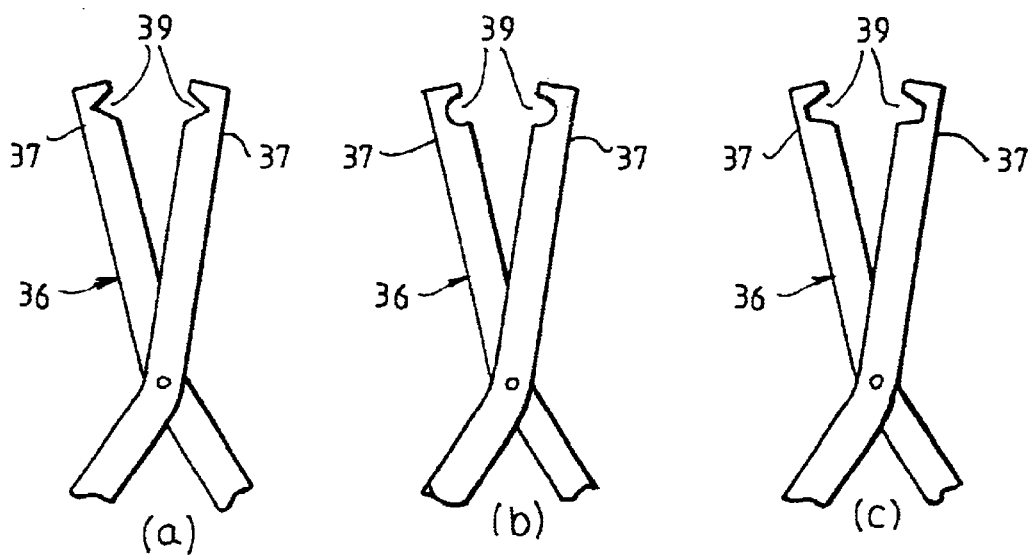
FIGS. 5(a) to (c) depict three different embodiments of a forming apparatus for use in the invention.
Figure 7:
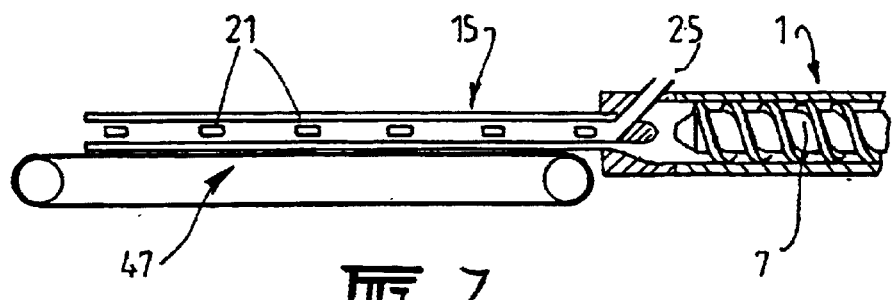
FIGS. 7–9 depict sequential stages of a capsule-coating process and system utilising a fourth embodiment of the invention.
Figure 8:
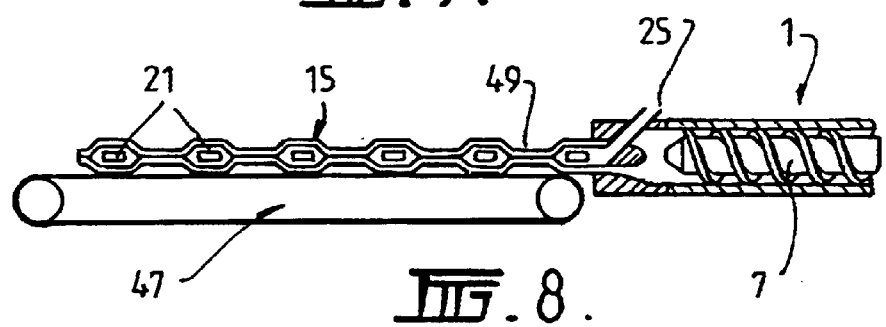

Desirably, the manufacture of sealed containers (such as the one schematically depicted in FIG. 10) would be produced by an automated or partly automated process capable of being performed on a continuous or repeated basis, so that many such sealed containers could be conveniently produced by operating the process. Such a process is depicted schematically in FIGS. 7–9. As shown in FIG. 7, a coating structure 15 (which when viewed in three dimensions, would have a generally tubular structure) is extruded from a forming apparatus 1 (shown in enlarged view in FIG. 4) onto a conveyor belt 47. Multiple units of a core material 21 (which might take the form of a pharmaceutical tablet) are rear loaded into the internal cavity 17 of the extruded core structure 15, via a sleeve 25. As shown in FIG. 8, a first compression means 49 compresses the coating structure 15 between each of the locations where a unit of the core material 21 has been deposited. This causes opposed surfaces of the coating structure 15 to be brought together, by effectively "pinching" them. This first step of compression may occur shortly after the coating structure 15 exits the forming apparatus 1, so as to ensure that the core material 21 is properly retained within the coating structure. This might be important where, for example, the coating structure 15 is extruded downwardly from the forming apparatus, so that if compression of the coating structure were not to occur at that point, the coating material would fall out of the coating structure, under the influence of gravity. Such an Q arrangement is depicted in FIG. 1.

Figure 9:
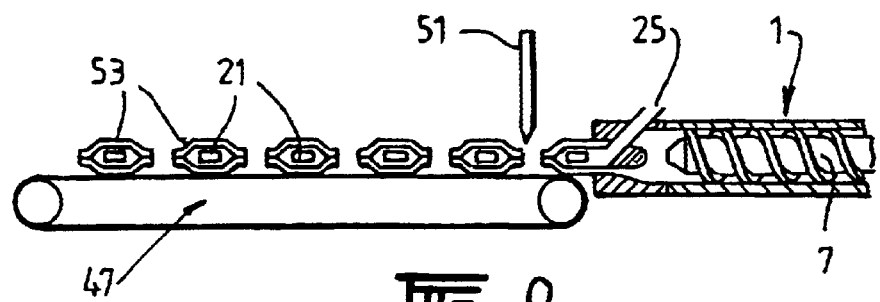

As shown more particularly in FIG. 9, a subsequent compression is then performed on the extruded coating structure, at a second location, by a second compression means 51. In the process depicted in FIG. 9, the second compression means takes the form of an apparatus which both compresses the coating structure, and at the same time cuts it, so as to form individual capsules (each denoted 53), which are conveyed by the conveyor belt to be further processed as desired according to the particular application to which they are to be put. Such further processing might, for example, take the form of heating the ends of the capsules so as to seal them more effectively, if so required for any particular application. (4)

Many variations of the process described above can of course be made, without departing from the general concept of the invention. For example, an automated processing system embodying the inventive concept could include more than two compression/cutting mechanisms, to achieve production efficiencies. Further, the profile of the filled coating structure could be collapsed between individual units of the core material contained within it, by restricting the ingress of air. This could be achieved, for example, by limiting the ingress of air into the cavity of the coating structure at predetermined times in the performance of the process (typically, between the insertion of units of the core material). This might aid the process of sealing individual coated structures. The cutting and sealing of loaded sections from a length of extrudate could be achieved with a blade (either cold or heated), a saw, a pinching mechanism, or a non-mechanical cutter, such as a laser. The appropriate cutting and sealing mechanism(s) would be chosen to suit the particular application.

Co-ordination of the various process steps involved in producing coated structures such as those described above could be achieved by any suitable means, including mechanical means (eg where the movement of all moving parts is mechanically synchronised), or by electro-mechanical means (where the motion of moving parts is controlled electronically from sensors appropriately positioned to detect the status of the various stages of the process). Hydraulic or pneumatic components used in the apparatus and process could conveniently be controlled in this manner. In many modem manufacturing plants, the process would additionally be controlled by computerised means.

The sealed structures produced by the method and apparatus aspects of the invention could take many forms, and could be produced in a broad variety of sizes and dimensions (including conceptually, even micro and even nano-particulate sizes). Such containers could be put to a broad variety of uses, and it is to be understood that invention is by no means limited to the pharmaceutical applications which have been discussed earlier in this specification. For example, sealed containers made in accordance with the apparatus and method aspects of the invention could be used to encapsulate transponders for injection into animals, for veterinary identification. Further, such coated structures could also be used for producing controlled release devices for releasing agricultural chemicals into the environment (eg, for fertilising the growth of plants). It is therefore to be understood that the invention is capable of many modifications and/or variations, and that the spirit and scope of the invention is by no means limited to the details of the preferred embodiments described earlier. It is therefore to be understood that the spirit and scope of the invention extends to every novel feature and combination of features disclosed herein.

EXAMPLES

The following non-limiting examples of the invention are given below.

A. In Vitro Experiments

In a first set of experiments, the applicants prepared controlled release containers in accordance with the method aspect of the invention, and measured the latency of release from those containers, of a bioactive release "marker"

(Methylene Blue) in an in vitro setting approximating typical physiological conditions in a mammalian species. The details of the experiments conducted and the results obtained from them are set out below.

In the experiments, four (4) batches of "Resomer" coated tablets, approximately 25 mm in length and of 3 mm external diameter were produced for testing, as follows. (It should be noted that the term "Resomer" is a trade mark of the Boehringer Ingelheim corporate group).

Materials Used:
Polymers
Polymer formulations used were:
 1 R206 (as supplied by manufacturer);
 2 RG858 (as supplied by manufacturer);
 3 RG506 (as supplied by manufacturer); and
 4 RG504 (as supplied by manufacturer).

(The "manufacturer" was the Boehringer Ingelheim corporate group).

Resomer poly-d,l-lactide, R206 (i.v.=1.0; 200 g: Batch #241888) was obtained from Boehringer Ingelheim.

Resomer 85:15 poly-d,l-lactide-co-glycolide copolymer, RG858 (i.v.=1.4; 200 g: Batch #261073) was obtained from Boehringer Ingelheim.

Resomer 50:50 poly-d,l-lactide-co-glycolide copolymer, RG506 (i.v.=0.8; 200 g: Batch #34034) was obtained from Boehringer Ingelheim.

Resomer 50:50 poly-d,l-lactide-co-glycolide copolymer, RG504 (i.v=0.4; 200 g: Batch #34015) was obtained from Boehringer Ingelheim.

Chloroform (HPLC grade) was from BDH (Hypersolv).

All other chemicals and reagents were generally analytical reagent grade.

Gel Permeation Chromatography (GPC)

Gel Permeation High Performance liquid chromatographic analysis was used to confirm the repeatability of production of controlled release devices using the apparatus and method aspects of the invention.

The GPC-HPLC system consisted of a Hewlett Packard 1050 series pump and auto-sampler. This was connected with a series of Hewlett-Packard and PLgel columns (polystyrene-divinylbenzene), consisting of one PLgel 10 $\mu$m mixed-B (#10 $\mu$MIXB8434) and two HP/PLgel 5 $\mu$m mixed-D columns (#'s 5$\mu$48879 and 5$\mu$523413), 300×7.5 mm each, and a PLgel guard column (5 $\mu$m; 5×100 mm). A Sedex 55 Evaporative Light Scattering detector operating at a temperature of 35 degrees Celsius with nitrogen gas purge/nebuliser was used for peak detection. The system was run isocratically with chloroform as the mobile phase at a flow rate of 1.0 ml/min.

Samples of polymer extrudate were prepared for molecular weight analysis using Gel Permeation Chromatography (GPC) by dissolving the sample (about 20 mg) in chloroform (1.0 ml). Samples (400 $\mu$l) were then placed in autosampler vials containing a Flow Rate Marker ("FRM"; 25 $\mu$l), sealed and then run through the HPLC system. The sample injection volume was 10 $\mu$l.

Molecular weights ($M_n$ and $M_w$) were calculated from data acquired by Hewlett Packard Chem Station Software and treated using proprietary GPC analysis software after setting integration limits manually. Calibration used a series of polystyrene standards ($M_r$: 2880000, 1290000, 560000, 66000 and 10100 atomic mass units ("amu")). The polydispersities of the standards were 1.03–1.06 for all standards. Standard samples were run subsequent to every sixth or seventh sample.

GPC Data Analysis:

GPC data analysis entailed the following procedure:
 raw data files in HPChem Station format were downloaded for importation into the proprietary GPC analysis software;
 the standards from each run were analysed to ensure no anomalous occurrences had arisen during the chromatographic run. The latter was determined as follows.
  comparison of the Peak Volume and Peak molecular weight for each of the standard samples; followed by use of the first standard for column calibration to optimise the analysis algorithm; with
  the molecular weights of each of the standards, including the first standard, then being determined using the calibrated column data.

The molecular weight of the analysis samples was then calculated using the column calibration algorithm established from the appropriate groups of standards.

Extrusion

Processing was performed on a Brabender Extruder at the CASEY Centre for Polymer Technology, Dandenong, Victoria, Australia. The equipment used consisted of the following:
 Brabender Extruder—Plasticorder Type PL2000-6 consisting of
 Dynamometer (Model No. 814400)
 Interface (Model No. 680118104)
 Temperature Controller (Model No. 680147)
 Single Screw Attachment Type 19/25D
 Haul Off (Model No. 297828)
Crosshead Die Assembly.

The conditions typically used for extrusion of the d,l-polylactide-co-glycolide polymers are given in Table I below. The procedure for setup and extrusion involved the following:
 1 When the temperatures had stabilised in the apparatus, the extruder barrel was purged with Ethylene vinyl acetate (EVA). When the purge material appeared clear of any contaminant the barrel was left to run empty.
 2 The screw and haul-off belt speeds were then set appropriately for the material.
 3 Polymer was loaded into the feed throat and pushed, stuffed or starve fed as required.
 4 Air cooling of the extrudate was set up as required.
 5 The first material through was assumed to be contaminated with purge polymer and was discarded (approximately the first 50 grams).
 6 The resultant polymer extrudate was then hauled off. The extruder was then run to empty.

TABLE 1

Brabender Extruder Conditions

| Polymer | ID | Zone 1° C. | Zone 2° C. | Zone 3° C. | Die ° C. | rpm |
|---|---|---|---|---|---|---|
| d,l-pLa | R206 | 90 | 110 | 125 | 130 | 35 |
| d,l-pLa/pGa (85:15) | RG858 | 110 | 125 | 140 | 165 | 10 |
| d,l-pLa/pGa (50:50) | RG506 | 90 | 110 | 125 | 130 | 35 |
| d,l-pLa/pGa (50:50) | RG504 | 90 | 110 | 125 | 130 | 20 |

The extrusion conditions for these process runs were dependent on the individual polymer characteristics.

However, the data contained in Table 1 indicate the conditions generally used.

Each of the four runs progressed relatively smoothly, having stabilized virtually immediately following commencement of the extrusion process. It was observed that samples from the beginning to the end of the extrusion run exhibited similar weight average ($M_w$) and number average ($M_n$) molecular weights. The mean molecular weights, relative to polystyrene, for the selected samples are presented in Table 2.

TABLE 2

Formulation Details

| Unit Code | Formulation | Samples Prepared | Average Molecular Weight of Selected Samples | | Polydispersity |
|---|---|---|---|---|---|
| | | | $M^n$ | $M^w$ | |
| 1 | Resomer R206 | 160 | 47300 | 120833 | 2.6 |
| 2 | Resomer RG858 | 160 | 156500 | 260167 | 1.7 |
| 3 | Resomer RG506 | 160 | 31850 | 91808 | 2.9 |
| 4 | Resomer RG504 | 160 | 5080 | 17725 | 3.5 |

In Vitro Performance Monitoring

Samples were placed in approximately 20 ml of phosphate buffered saline, (pH 7.2), and held at 37 degrees Celsius. The samples were checked daily. Checking involved some agitation of the solution/suspension, albeit not vigorous enough to induce mechanical damage. Release of the bioactive marker from any test sample was determined by visual inspection (namely, by the solution turning blue).

Results:

Polymer Extrusion

Polymer extrusion with the Brabender extruder proceeded under conditions, and in a manner, consistent with materials of comparable composition. Each of the four runs progressed smoothly. GPC-HPLC data indicated that the extrudate exhibited similar weight average molecular weights throughout the runs. The mean molecular weight of the extrudate was, in general, equivalent to 90% of the molecular weight of the starting materials indicating minimal thermal degradation had been induced.

(B) In Vivo Studies

Outline of Experiments Conducted

The studies set out in A (above) confirm the suitability of controlled release devices made in accordance with the invention, in an in vitro environment. The applicants also conducted studies to confirm that the invention could be used to produce devices suitable for use as controlled release delivery devices in vivo. These further studies are discussed below.

The general nature of the experiment was as follows. Rats were randomly selected into two groups. The first group (Group B) received administration of an Avidin formulation. The second group (Group A) was administered the same Avidin formulation, however, presented in the form of a controlled release delivery device made in accordance with the invention. The time delay to the appearance of antibodies in each group to the Avidin formulation, was measured. The experimental details were as follows.

Avidin Formulation

The Avidin formulation used had the following composition:

| | |
|---|---|
| Avidin | 5 mg/35 mg |
| Lactose | 95.56% (w/w) |
| Magnesium Stearate | 3% (w/w) |
| Explotab (Sodium start glycolate) | (1.94% w/w) |

Preparation of Implants

Controlled release delivery devices containing the Avidin formulation were made as follows. Avidin tablets weighing 25 mg were coated using a plastics extrusion apparatus into which 50:50 poly-d,l-lactide-co-glycolide copolymer had been melt processed, so as to form individual coated tablets, of approximately 12 mm length and 3.5 mm diameter, in accordance with the method aspect of the invention.

Animals

Rats (Sprague-Dawley; Male; 20), mean mass=254 (Stdevp=36 g) were employed for the experiment (two randomly selected groups of ten for testing of response to antigen).

All animals were given free access to food (Barastoc rodent pellets) and water at all times during the study. All animals were inspected daily by the animal house supervisor, and thrice weekly for detailed observation by the applicants' personnel to ensure no adverse/traumatic reactions to the implanting or implants arose.

Animals were identified using permanent colour marker pens and marking the animals on the tail.

Test Groups

The dose regimens applied to the two experimental groups were as follows:

| |
|---|
| Group A: delayed release "Avidin" (10 animals) |
| Group B: "Avidin" only (10 animals) |

Implantation

Rats were implanted by means of a modified Synovex® implanting gun. Animals were not anaesthetised. The implantation site was shaven, then washed with ethanol (70% v/v) prior to implantation. The implant puncture wound required no surgical closure.

Subsequent to implantation, all animals were observed for trauma and/or abnormal behaviour for 180 minutes. No abnormal behaviour was observed during this period. Minimal wound bleeding was observed during the observation period. Examination of the animals 24 hours after implantation showed all wounds had sealed with no signs of infection.

ELISA Testing Protocol

Nunc "Immuno" Microtitre plates were coated with 30 μl of antigen (Avidin stock solution; 10 mg/ml) at 5–50 μg/ml in 0.04 M carbonate coating buffer. The plates were incubated at 37° C. for 1 hour.

Control test groups of the following composition were run with the test serum:

No antigen, Antibody, Horse Radish Peroxidase (HRP), TMB

No antigen, No antibody, No HRP, TMB

Antigen, No antibody, HRP/TMB

Antigen, known positive antibody, HRP/TMB

Coated plates were washed with water (3×) or saline/Tween 20.

Unbound sites were blocked by incubating for 60 minutes at 37° C. using 300 µl/well of 1% BSA in PBS plus 0.1% Tween 20 in PBS.

"Blocked" plates were washed (3×) with saline/Tween 20.

Test serum samples (50 µl) diluted 1 in 200 in blocking solution were added to test wells and incubated at 37° C. for 90 minutes.

"Test" plates were washed (3×) with saline/Tween 20.

Anti-rat conjugated HRP (RAM-HRP; 50 µl/well) diluted I in 1000 in blocking solution was added and the plates incubated under ambient conditions for 120 minutes.

Plates were washed (3×) with saline/Fween 20.

The reaction was initiated by addition of TMB (100 µl/well). Plates were held in a humid box for 60 minutes.

The reaction was terminated by addition of sulphuric acid (2.0 M; 50 µl/well). Plates were held in a humid box for 60 minutes.

Absorbance readings were taken using a Multiscan plate reader using Filter 1=4=450 nm and Filter 2=8=690 nm.

Results:

Observations

TABLE 4

| x Group | 10 Nov. 1997 | 17 Nov. 1997 | 24 Nov. 1997 | 01 Dec. 1997 | 08 Dec. 1997 | 15 Dec. 1997 | 17 Dec. 1997 |
|---|---|---|---|---|---|---|---|
| Mean Group A | 0.097 | 0.094 | 0.121 | 0.115 | 0.284 | 0.428 | 0.490 |
| Mean Group B | 0.095 | 0.131 | 0.518 | 0.612 | 0.681 | 0.677 | 0.622 |
| Stdevp Group A | 0.007 | 0.010 | 0.013 | 0.007 | 0.307 | 0.422 | 0.413 |
| Stdevp Group B | 0.008 | 0.038 | 0.309 | 0.359 | 0.391 | 0.383 | 0.392 |
| t-test significance values (p) | 0.65 | 0.02 | 0.0039 | 0.0025 | 0.028 | 0.21 | 0.5 |

The data set out above are represented graphically in FIG. 11 of the drawings.

Conclusions

These data show a marked delay in the seroconversion of rats in Group A, relative to those of Group B. When analysed using Student's t-Test, a statistically significant difference between the data for the two groups was found at 7, 14, 21 and 28 days following administration of the formulations to the animals (ie, between Nov. 17, 1997 and Dec. 8, 1997). Subsequent to Dec. 8, 1997, the immune response of the animals in the respective groups showed no statistically significant difference, suggesting that seroconversion in Group A animals had simply been delayed, and was reaching a similar response level to that observed earlier in Group B. The seroconversion of rats treated with the controlled release devices of the invention was therefore delayed—on a statistically significant basis—relative to the delay observed in the Group B rats.

The claims defining the invention are as follows:

1. A method of producing a delivery device for the controlled release of a bioactive substance, which comprises the steps of:
    (a) forming a generally elongate structure by melt processing extrusion and extrusion when heated of one or more pharmaceutically or veterinarily acceptable polymeric materials so as to coat a core material containing the bioactive substance, the coating structure having an internal cavity extending at least substantially along its length, and wherein, the internal cavity of the coating structure is capable of receiving the core material;
    (b) inserting the core material into the internal cavity of the coating structure;
    (c) compressing the coating structure at a first location along its length so as to generally form a seal at that location; and
    (d) compressing the coating structure at a second location along its length.
2. A method as claimed in claim 1, wherein the one or more pharmaceutically or veterinarily acceptable polymeric materials comprise materials which are degradable.
3. A method as claimed in claim 2, wherein the coating structure is formed as a single layer.
4. A method as claimed in claim 2, wherein the coating structure comprises two or more layers.
5. A method as claimed in claim 4, wherein the two or more layers are layers of the same material.
6. A method as claimed in claim 4, wherein the two or more layers are layers of two or more different materials.
7. A method as claimed in claim 1, wherein the pharmaceutically or veterinarily acceptable polymeric material or materials are selected from the group consisting of:
    (a) polylactide co-glycolide polymers;
    (b) polyesters;
    (c) polysaccharides;
    (d) polyamides;
    (e) poly (amino acids);
    (f) poly (ortho esters);
    (g) polyanhydrides;
    (h) polyphosphoesters;
    (i) polymers formed through the combination of chemical bonds; and
    (j) combinations of two or more of (a) to (i).
8. The method of claim 7, wherein the polymers of group (i) comprise:
    (a) pseudo-peptides;
    (b) poly (phosphoester-urethanes)
    (c) polydepsipeptides; and
    (d) combinations thereof.
9. A method as claimed in claim 1, wherein the core material comprises:
    (a) a tablet;
    (b) a gel;
    (c) a paste;
    (d) granules;
    (e) powder;
    (f) a fluid; or
    (g) combinations of two or more of (a) to (f).
10. A method as claimed in claim 1, wherein the core material comprises:
    (a) a bioactive substance selected from the group consisting of:
        (1) natural, synthetic or recombinant pharmacological agents;
        (2) food additives;
        (3) food supplements;
        (4) antigens;
        (5) antibodies;
        (6) cytokines;
        (7) growth promotants;
        (8) hormones;
        (9) vaccines;
        (10) cancer cell inhibitory agents;
        (11) immuno-suppressants;

(12) immuno-stimulants;
(13) antimicrobial agents;
(14) anti-viral agents;
(15) vitamins;
(16) minerals;
(17) organic nutrients;
(18) inorganic nutrients; and
(19) combinations of two or more of the aforegoing; and (b) optionally, one or more pharmaceutically or veterinarily acceptable carriers and/or excipients.

11. A method as claimed in claim 1, wherein the step of compressing the coating structure at the first location along its length so as generally to form a seal at that location comprises the step of bringing two or more mutually opposed surfaces of the coating structure into contact with one another, so as generally to form a seal at that location.

12. A method as claimed in claim 11, wherein the step of compressing the coating structure at the first location along its length comprises cutting the coating structure at that location.

13. A method as claimed in claim 1, wherein the step of compressing the coating structure at the second location along its length so as to generally form a seal at that location comprises the step of bringing two or more mutually opposed surfaces of the coating structure into contact with one another, so as to form a seal at that location.

14. A method as claimed in claim 1, wherein the step of compressing the coating structure at the second location along its length does not give rise to the formation of a seal at that location.

15. A method as claimed in claim 13, wherein the step of compressing the coating structure at the second location along its length comprises cutting the coating structure at that location.

16. A method as claimed in claim 13, wherein a generally sealed container is formed.

17. A method as claimed in claim 14, wherein a container is formed which is generally sealed at one of two mutually opposed ends thereof, but not at the other end.

18. A method as claimed in claim 1, wherein steps (a) to (d) are repeated along the length of the coating structure, so as to produce a plurality of coated structures in the form of controlled release delivery devices for a bioactive substance.

19. A method as claimed in claim 18, additionally comprising automating the repeated performance of the method along the length of the coating structure.

20. The method as claimed in claim 1, wherein the method comprises performing steps (a) to (d) sequentially.

21. The method as claimed in claim 1, wherein the method comprises performing steps (a) to (d) non-sequentially.

22. The method as claimed in claim 21, wherein said non-sequential steps are performed as follows:

(i) step (a) is the first step;
(ii) step (c) is the second step;
(iii) step (b) is the third step; and
(iv) step (d) is the fourth step.

* * * * *